US008879062B2

(12) United States Patent
Ikeda

(10) Patent No.: US 8,879,062 B2
(45) Date of Patent: Nov. 4, 2014

(54) ANALYSIS APPARATUS AND ANALYSIS METHOD

(71) Applicant: Imagineering, Inc., Kobe (JP)

(72) Inventor: Yuji Ikeda, Kobe (JP)

(73) Assignee: Imagineering, Inc., Hyogo (JP)

( * ) Notice: Subject to any disclaimer, the term of this patent is extended or adjusted under 35 U.S.C. 154(b) by 0 days.

(21) Appl. No.: 13/839,748

(22) Filed: Mar. 15, 2013

(65) Prior Publication Data

US 2013/0208274 A1 Aug. 15, 2013

Related U.S. Application Data

(63) Continuation of application No. PCT/JP2011/070773, filed on Sep. 12, 2011.

(30) Foreign Application Priority Data

Sep. 15, 2010 (JP) ................................. 2010-207384

(51) Int. Cl.
*G01J 3/30* (2006.01)
*G01N 21/71* (2006.01)
*G01N 21/68* (2006.01)
*G01N 21/73* (2006.01)

(52) U.S. Cl.
CPC .............. *G01N 21/73* (2013.01); *G01N 21/718* (2013.01); *G01N 21/68* (2013.01)
USPC ........................................................ 356/316

(58) Field of Classification Search
USPC ........................................................ 356/316
See application file for complete search history.

(56) References Cited

U.S. PATENT DOCUMENTS 6,008,897 A * 12/1999 Sabsabi et al. ................ 356/318
7,821,634 B2 * 10/2010 Dillon et al. .................. 356/318
2012/0008139 A1 * 1/2012 Miziolek et al. .............. 356/318

OTHER PUBLICATIONS

Masashi Kaneko et al., "Microwave Assisted Spark Induced Breakdown Spectroscopy", Preprints of Meeting on Automotive Engineers, May 20, 2009, No. 18-09, pp. 1-4 (with partial English translation).
International Preliminary Report on Patentability dated Apr. 9, 2013 issued in corresponding application No. PCT/JP2011/070773.

* cited by examiner

*Primary Examiner* — Abdullahi Nur
(74) *Attorney, Agent, or Firm* — Westerman, Hattori, Daniels & Adrian, LLP

(57) ABSTRACT

An analysis apparatus includes a plasma generation unit and an optical analysis unit. The plasma generation unit generates initial plasma by momentarily energizing a target substance to be turned into a plasma state, and maintains the target substance in the plasma state by irradiating the initial plasma with an electromagnetic wave for a predetermined period of time. The optical analysis unit identifies the target substance based on information with respect to emission intensity during a period from when the emission intensity reaches a peak due to the initial plasma until when the emission intensity increases and reaches approximately a constant value due to electromagnetic wave plasma maintained by the electromagnetic wave, or information with respect to emission intensity after the electromagnetic wave irradiation is terminated.

4 Claims, 7 Drawing Sheets

ANALYSIS APPARATUS AND ANALYSIS METHOD

TECHNICAL FIELD

The present invention relates to an analysis apparatus and an analysis method for analyzing a target substance by analyzing light emitted from plasma.

BACKGROUND ART

Conventionally, there is known an analysis apparatus and an analysis method for analyzing a target substance by analyzing light emitted from plasma. For example, Japanese Unexamined Patent Application, Publication No. 2010-38560 discloses an analysis apparatus of this kind.

More particularly, Japanese Unexamined Patent Application, Publication No. 2010-38560 discloses an element analysis apparatus which employs laser-induced breakdown spectroscopy. In the element analysis apparatus, laser pulses are emitted from a laser oscillator and condensed on a sample surface, thereby turning a part of the sample surface into plasma. Constituent elements of the sample surface are turned into excited state atoms. The excited state atoms emit fluorescence when transiting to a lower level. The emitted fluorescence is incident upon a fluorescence detector via an optical fiber. The fluorescence detector converts information with respect to a wavelength of the fluorescence and intensity at the wavelength into electrical signals. A computer for measurement control performs element analysis based on the resultant electrical signals.

THE DISCLOSURE OF THE INVENTION

Problems to be Solved by the Invention

In the conventional analysis apparatuses such as described above, spectroscopic analysis of light emitted from plasma (hereinafter, referred to as "plasma light") has been employed to find wavelength components with high intensity so as to analyze a target substance. The inventor of the present invention, however, found out that it is possible to analyze a target substance by observing the variation in emission intensity of the plasma light while the plasma is being formed.

The present invention has been made in view of the above described circumstances, and it is an object of the present invention to provide an analysis apparatus for analyzing a target substance by analyzing plasma light emitted from plasma, wherein the analysis apparatus analyzes the target substance based on variation in emission intensity of the plasma light while the plasma is being formed.

Means for Solving the Problems

In accordance with a first aspect of the present invention, there is provided an analysis apparatus including: a plasma generation unit that generates initial plasma by momentarily energizing a target substance to be turned into a plasma state, and maintains the target substance in the plasma state by irradiating the initial plasma with an electromagnetic wave for a predetermined period of time; and an optical analysis unit that identifies the target substance based on information with respect to emission intensity during a period from when the emission intensity reaches a peak due to the initial plasma until when the emission intensity increases and reaches approximately a constant value due to electromagnetic wave plasma maintained by the electromagnetic wave, or information with respect to emission intensity after the electromagnetic wave irradiation is terminated.

According to the first aspect of the present invention, the plasma generation unit momentarily energizes the target substance to generate the initial plasma and irradiates the initial plasma with the electromagnetic wave to maintain the plasma state. Here, as shown in FIG. 3, which illustrates time series variation in emission intensity of the plasma light emitted from the plasma while the plasma is being formed, firstly, the momentary peak of emission intensity occurs due to the initial plasma, and subsequently, the emission intensity temporarily drops to a minimum value. Then, after reaching the minimum value, the emission intensity increases again due to the electromagnetic wave plasma and, after the electromagnetic wave irradiation is terminated, the emission intensity decreases to zero. The inventor of the present invention found out that different types of substance yield different results such as, for example, a delay time Ts of emission from the electromagnetic wave plasma in relation to the emission from the initial plasma, an increase rate $\Delta I/\Delta t$ of emission intensity per unit time when the emission intensity increases due to the electromagnetic wave plasma immediately after the emission from the initial plasma, a period of time from when the electromagnetic wave irradiation is terminated until when the emission intensity decreases to zero, and a decrease rate of emission intensity per unit time after the electromagnetic wave irradiation is terminated. Different types of substance yield different variation in emission intensity during the period from when the emission intensity of the initial plasma has the peak until when the emission intensity increases and reaches approximately a constant value due to the electromagnetic wave plasma, and different variation in emission intensity after the electromagnetic wave irradiation is terminated. Therefore, according to the first aspect of the present invention, the optical analysis unit identifies the target substance based on information with respect to emission intensity during the period from when the emission intensity reaches a peak due to the initial plasma until when the emission intensity increases and reaches approximately a constant value due to the electromagnetic wave plasma, or information with respect to emission intensity after the electromagnetic wave irradiation is terminated.

In accordance with a second aspect of the present invention, in addition to the feature of the first aspect of the present invention, the optical analysis unit identifies the target substance based on the delay time of the emission from the electromagnetic wave plasma in relation to the emission from the initial plasma.

According to the second aspect of the present invention, the target substance is identified based on the delay time Ts of the emission from the electromagnetic wave plasma in relation to the emission from the initial plasma.

In accordance with a third aspect of the present invention, in addition to the feature of the first or second aspect of the present invention, the optical analysis unit identifies the target substance based on increase rate of emission intensity per unit time when the emission intensity increases due to the electromagnetic wave plasma immediately after the emission from the initial plasma.

According to the third aspect of the present invention, the target substance is identified based on the increase rate $\Delta I/\Delta t$ of emission intensity per unit time when the emission intensity increases due to the electromagnetic wave plasma immediately after the emission from the initial plasma. This means that the target substance is identified based on a gradient of a graph (see FIG. 3) of emission intensity when the emission intensity increases due to the electromagnetic wave plasma immediately after the emission from the initial plasma.

In accordance with a fourth aspect of the present invention, there is provided an analysis apparatus. The analysis apparatus is provided with a plasma generation unit that energizes a target substance contained in a fluid and turns the target substance into a plasma state. The analysis apparatus is also provided with an optical analysis unit that detects at least one of concentration and quantity of the target substance based on variation rate of emission intensity per unit time of emission from the plasma generated by the plasma generation unit at a wavelength corresponding to the target substance.

According to the fourth aspect of the present invention, at least one of concentration and quantity of the target substance is detected based on the variation (regardless whether increase or decrease) in rate of emission intensity per unit time of the plasma light at the wavelength corresponding to the target substance. In a case in which a specific target substance is turned into plasma, variation rate of emission intensity per unit time differs depending on concentration and quantity of the target substance at the wavelength corresponding to the target substance from among wavelength components contained in the plasma light. The variation rate decreases as the concentration of the target substance increases. Also, the variation rate decreases as the quantity of the target substance increases. This leads to the fact that it is possible to detect concentration and quantity of the target substance based on the variation rate of emission intensity per unit time at the wavelength corresponding to the target substance. Therefore, according to the fourth aspect of the present invention, at least one of concentration and quantity of the target substance is detected based on the variation rate of emission intensity per unit time of the plasma light at the wavelength corresponding to the target substance.

In accordance with a fifth aspect of the present invention, in addition to the feature of the fourth aspect of the present invention, the plasma generation unit is provided with an initial plasma generation unit that energizes the target substance and turns the target substance into a plasma state, and a plasma maintenance unit that irradiates the initial plasma generated by the initial plasma generation unit with an electromagnetic wave for a predetermined period of time and maintains the target substance in the plasma state. The optical analysis unit detects concentration or quantity of the target substance based on decrease rate of emission intensity per unit time when the plasma vanishes after the plasma maintenance unit terminates the electromagnetic wave irradiation.

According to the fifth aspect of the present invention, at least one of concentration and quantity of the target substance is detected based on the decrease rate of emission intensity per unit time when the plasma vanishes after the plasma maintenance unit terminates the electromagnetic wave irradiation.

In accordance with a sixth aspect of the present invention, there is provided an analysis method including: a plasma generation step of generating initial plasma by momentarily energizing a target substance to be turned into a plasma state, and maintaining the target substance in the plasma state by irradiating the initial plasma with an electromagnetic wave for a predetermined period of time; and an optical analysis step of identifying the target substance based on information with respect to emission intensity during a period from when the emission intensity reaches a peak due to the initial plasma until when the emission intensity increases and reaches approximately a constant value due to electromagnetic wave plasma maintained by the electromagnetic wave, or information with respect to emission intensity after the electromagnetic wave irradiation is terminated.

In accordance with a seventh aspect of the present invention, there is provided an analysis method including: a plasma generation step of energizing a target substance contained in a fluid and turning the target substance into a plasma state; and an optical analysis step of detecting at least one of concentration and quantity of the target substance based on variation rate of emission intensity per unit time of emission from the plasma generated by the plasma generation unit at a wavelength corresponding to the target substance.

Effect of the Invention

According to the first, second, third, and sixth aspects of the present invention, the target substance is identified based on information with respect to emission intensity during the period from when the emission intensity reaches a peak due to the initial plasma until when the emission intensity increases and becomes approximately constant due to the electromagnetic wave plasma, or information with respect to emission intensity after the electromagnetic wave irradiation is terminated, since different types of substance yield different variation in emission intensity during the period from when the emission intensity of the initial plasma reaches a peak until when the emission intensity increases and reaches approximately a constant value due to the electromagnetic wave plasma, and different variation in emission intensity after the electromagnetic wave irradiation is terminated. Accordingly, it is possible to realize an analysis apparatus that can identify the target substance based on variation in emission intensity of the plasma light while the plasma is being formed.

Furthermore, according to the fourth, fifth, and seventh aspects of the present invention, at least one of concentration and quantity of the target substance is detected based on variation rate of emission intensity per unit time of the plasma light at the wavelength corresponding to the target substance, since variation rate of emission intensity per unit time at the wavelength corresponding to the target substance differs depending on concentration and quantity of the target substance. Accordingly, it is possible to realize an analysis apparatus that can detect concentration and quantity of the target substance based on variation in emission intensity of the plasma light while the plasma is being formed.

BEST MODE FOR CARRYING OUT THE INVENTION

In the following, a detailed description will be given of the embodiments of the present invention with reference to drawings. It should be noted that the following embodiments are merely preferable examples, and do not limit the scope of the present invention, applied field thereof, or application thereof.

<First Embodiment>

Figure 1:
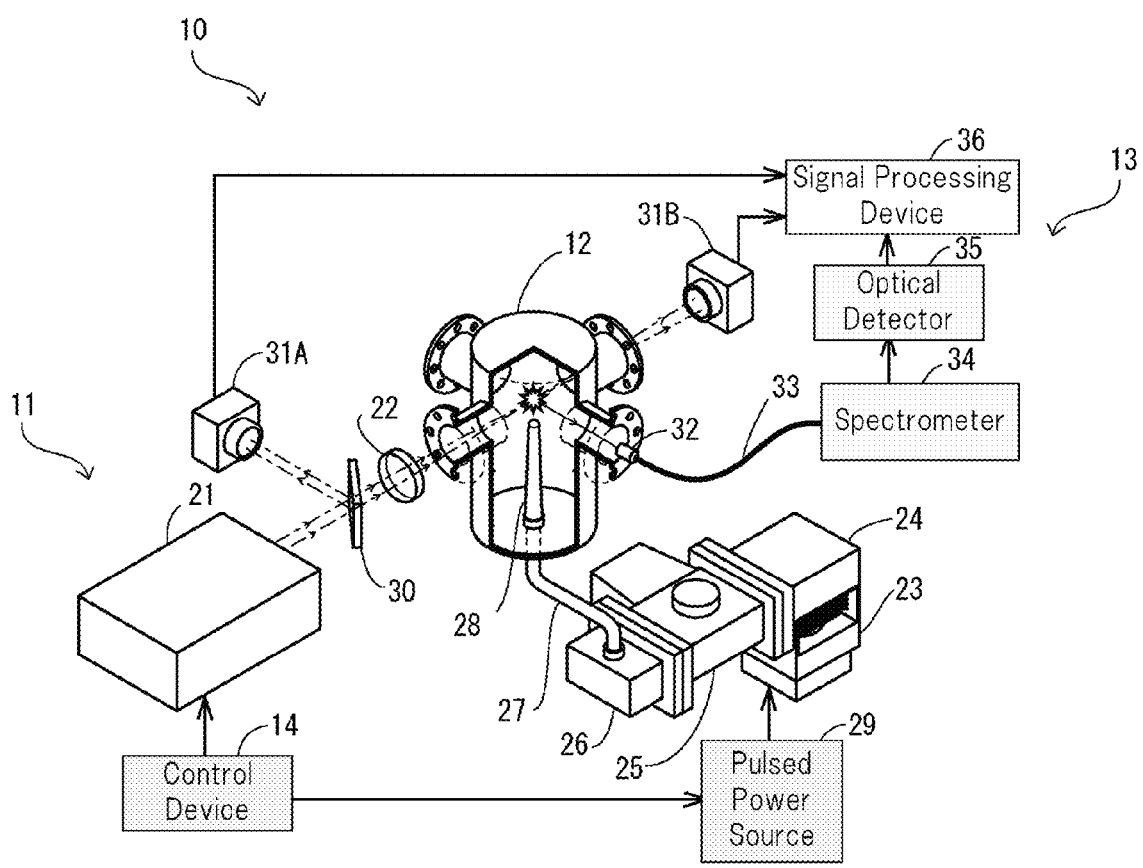
FIG. 1 is a schematic configuration diagram of an analysis apparatus according to a first embodiment.

As shown in FIG. 1, an analysis apparatus 10 according to a first embodiment is provided with a plasma generation device 11, a cavity 12, an optical analysis device 13, and a control device 14. The control device 14 controls the plasma generation device 11 and the optical analysis device 13. The analysis apparatus 10 according to the first embodiment can analyze any type of substance as the target substance regardless of whether the substance is in a state of solid, liquid, or gas, as long as the plasma generation device 11 can turn the substance into a plasma state.

Construction of Plasma Generation Device

The plasma generation device 11 includes a laser light source 21, a light collection optical system 22, a microwave oscillator 23, microwave transmission paths 24 to 27, an antenna 28, and a pulsed power source 29. The plasma generation device 11 constitutes a plasma generation unit that generates initial plasma by momentarily energizing a target substance 15 to be in a plasma state and maintains the plasma state by irradiating the initial plasma with an electromagnetic wave for a predetermined period of time. The laser light source 21 and the light collection optical system 22 constitute an initial plasma generation unit that energizes the target substance 15 and turns the target substance into a plasma state. The microwave oscillator 23, the microwave transmission paths 24 to 27, the antenna 28, and the pulsed power source 29 constitute a plasma maintenance unit that irradiates the initial plasma generated by the initial plasma generation unit with the electromagnetic wave for the predetermined period of time to maintain the plasma state.

The laser light source 21 oscillates a laser light, which can turn the target substance 15 into a plasma state. The laser light oscillated by the laser light source 21 passes through the light collection optical system 22 and is condensed on a focal point of the light collection optical system 22. The focal point of the light collection optical system 22 is located within the cavity 12. As the laser light source 21, for example, an Nd-YAG laser light source may be employed. As the light collection optical system 22, for example, a convex lens may be employed.

The plasma generation device 11 is configured so that energy density of the laser light condensed on the focal point of the light collection optical system 22 is not below a breakdown threshold value of the target substance 15. This means that the laser light is configured to have sufficient power to turn the target substance 15 located at the focal point into plasma.

The microwave oscillator 23 is connected to the antenna 28 via the microwave transmission paths 24 to 27. The microwave transmission paths 24 to 27 includes a waveguide 24 coupled to the microwave oscillator 23, an isolator 25 coupled to the waveguide 24, a coaxial-to-waveguide converter 26 coupled to the isolator 25, and a coaxial cable 27 coupled to the coaxial-to-waveguide converter 26. The microwave oscillator 23 is also connected to the pulsed power source 29. Upon receiving power supplied from the pulsed power source 29, the microwave oscillator 23 oscillates a microwave.

The antenna 28 is connected to the coaxial cable 27. A tip end of the antenna 28 is pointed at a focal point of the light collection optical system 22. The microwave oscillated by the microwave oscillator 23 is radiated from the antenna 28 toward the focal point of the light collection optical system 22 via the microwave transmission path 24 to 27.

As the microwave oscillator 23, for example, a magnetron that oscillates 2.45 GHz microwave may be employed. As the antenna 28, for example, a ¾ wavelength monopole antenna, which has a sufficient gain for the microwave oscillated by the microwave oscillator 23, may be employed. As the pulsed power source 29, for example, an inverter type power supply device may be employed.

The cavity 12 is an approximately cylindrical-shaped container having a resonance structure for the microwave and prevents the microwave from leaking outside. The cavity 12 is provided with a support member (not shown) that supports the target substance 15. The cavity 12 is provided with a light inlet window to let in the laser light oscillated by the laser light source 21. The laser light oscillated by the laser light source 21 is incident upon the cavity 12. Inside of the cavity 12, the target substance 15 turns into a plasma state due to the laser light. Also, inside of the cavity 12, the microwave is radiated from the antenna 28 to the target substance 15 in the plasma state.

Operation of Plasma Generation Device

The plasma generation device 11 performs a plasma generation and maintenance operation that turns the target substance 15 into a plasma state and maintains the target substance 15 in the plasma state, in accordance with an instruction from the control device 14.

In the plasma generation and maintenance operation, the pulsed power source 29, upon receiving a start signal outputted from the control device 14, starts to supply power to the microwave oscillator 23. As a result thereof, the microwave oscillator 23 starts to oscillate microwaves and the microwaves are radiated from the antenna 28 toward the target substance 15 in the cavity 12. In the cavity 12, the microwaves resonate to form a standing wave. In the vicinity of a surface of the target substance 15 irradiated with the laser, an antinode of the standing wave is formed, and thus, a strong electric field region is generated.

Subsequently, the laser light source 21, upon receiving an oscillation signal outputted from the control device 14, oscillates laser light of a single pulse. The laser light is oscillated immediately after the microwave irradiation starts. The laser light oscillated by the laser light source 21 is condensed on the surface of the target substance 15 via the light collection optical system 22. A high density energy is momentarily applied to the target substance 15.

Figure 2:
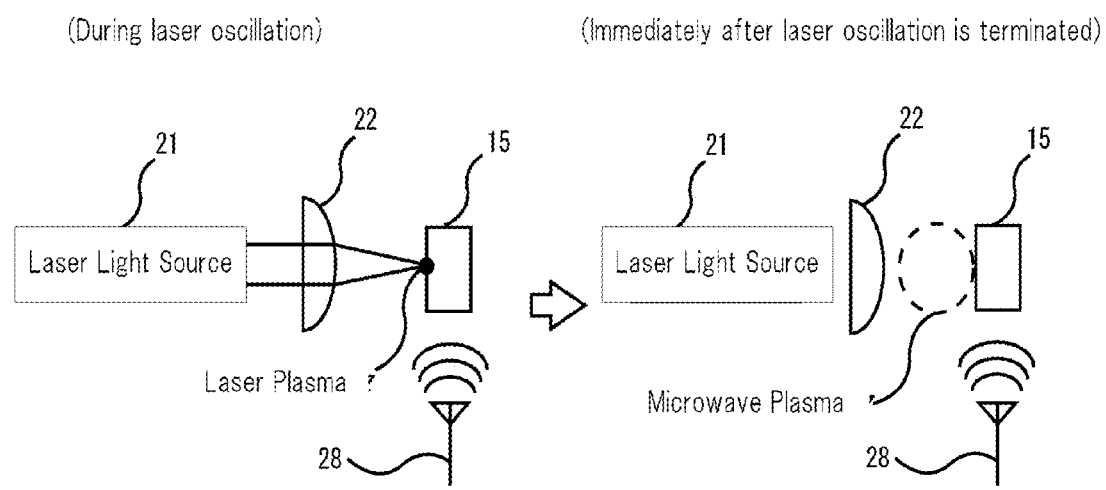
FIG. 2 is an explanatory diagram of a plasma generation and maintenance operation according to the first embodiment.

On the surface of the target substance 15 at a region irradiated with the laser light, energy density increases and exceeds the breakdown threshold value of the target substance 15. Then, as shown in FIG. 2, the substance at the region irradiated with the laser light is ionized and turned into a plasma state. This means that plasma is generated out of the target substance 15 as raw material. Hereinafter, the plasma generated by the laser light is referred to as "laser plasma". The laser plasma corresponds to the initial plasma.

Immediately after the laser oscillation is terminated, the microwave irradiation is still continued. Therefore, as shown in FIG. 2, the laser plasma absorbs the microwave energy and expands. The expanded plasma is maintained by the microwave. Hereinafter, the plasma maintained by the microwave is referred to as "microwave plasma". The microwave plasma corresponds to the electromagnetic wave plasma.

After that, the pulsed power source 29, upon receiving a termination signal outputted from the control device 14, stops supplying power to the microwave oscillator 23. As a result thereof, the microwave oscillator 23 terminates the microwave oscillation. The microwave oscillator 23 stops after the laser light is oscillated. The microwave irradiation terminates, for example, 5 seconds after the laser light oscillation is terminated. Consequently, electron recombination occurs, and the microwave plasma vanishes.

The pulsed power source 29 repeatedly supplies pulse waves (or burst waves) to the microwave oscillator 23 from when the pulsed power source 29 receives the start signal until when the pulsed power source 29 receives the termination signal. The pulsed power source 29 supplies power to the microwave oscillator 23 at a predetermined duty cycle (duty ratio of on and off). The microwave oscillator 23 repeats oscillation and non-oscillation of the microwave at the predetermined duty cycle. The microwave plasma is maintained as non-equilibrium plasma without becoming thermal plasma. In the first embodiment, the microwave oscillation starts at a point of time when the first pulse wave is received and terminates at a point of time when the last pulse wave is received. The period from when the start signal is received until when the termination signal is received is defined as a microwave irradiation period. The energy of microwave per unit time is maintained constant during the microwave irradiation period without any adjustment.

Although, in the first embodiment, timing to start the microwave oscillation is set before the laser light is oscillated, the timing to start the microwave oscillation may be set after the laser light is oscillated as long as the microwave oscillation starts before the laser plasma vanishes.

Figure 3:
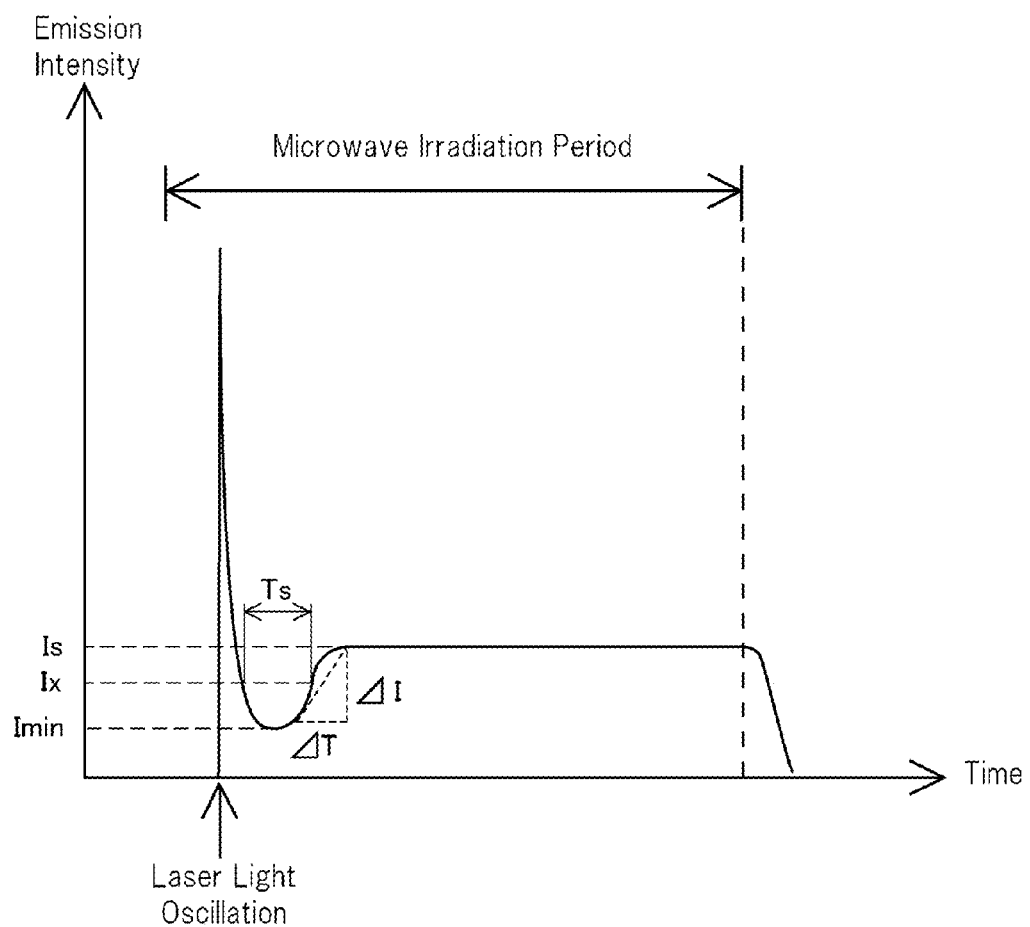
FIG. 3 is a graph showing time series variation in emission intensity of emission from plasma generated by a plasma generation device according to the first embodiment.

Here, as shown in FIG. 3, which illustrates time series variation in emission intensity of the plasma light emitted from the plasma while the plasma is being formed, firstly, the momentary peak of emission intensity occurs due to the laser plasma, and subsequently, the emission intensity drops to a minimum value, which is close to zero. After the emission intensity reaches the minimum value, the emission intensity increases again due to the microwave plasma, and then, maintains approximately at a constant value until the microwave plasma starts to vanish.

In the present specification, plasma formed until the emission intensity of the plasma reaches the minimum value immediately after the emission intensity of the plasma reaches the peak value due to the initial plasma is defined as the "laser plasma", and the plasma formed after the emission intensity of the plasma reaches the minimum value is defined as the "microwave plasma". In the first embodiment, the plasma generation device 11 is configured so that the laser plasma is higher in the maximum value of the emission intensity than the microwave plasma. The output powers of the laser light source 21 and the microwave oscillator 23 are configured so that the microwave plasma is higher in energy density than the laser plasma.

Construction of Optical Analysis Device

The optical analysis device 13 analyzes the plasma light emitted during the plasma generation and maintenance operation. The optical analysis device 13 constitutes an optical analysis unit that identifies the target substance 15 by using information with respect to the emission intensity during the period from when the emission intensity of the plasma reaches the peak value due to the initial plasma until the emission intensity increases and reaches approximately a constant value due to the microwave plasma.

The optical analysis device 13 includes a beam sampler 30, a first power meter 31A, a second power meter 31B, an optical element 32, an optical fiber 33, a spectrometer 34, an optical detector 35, and a signal processing device 36.

The beam sampler 30 is disposed between a laser light exit of the laser light source 21 and the light collection optical system 22. The beam sampler 30 separates a part of the laser light oscillated by the laser light source 21. The first power meter 31A receives the light separated by the beam sampler 30. An output signal from the first power meter 31A is inputted in the signal processing device 36. On the other hand, the second power meter 31B is disposed on an opposite side of the cavity 12 against the laser light source 21, and receives the laser light that has passed through the cavity 12. An output signal from the second power meter 31B is inputted in the signal processing device 36.

The optical element 32 is configured by a lens and the like, which light can be transmitted through. As the optical element 32, for example, a light collection optical system may be employed. In this case, the optical element 32 is disposed in such a manner that a focal point thereof is located at the region where the microwave plasma is formed.

The spectrometer 34 is connected to the optical element 32 via the optical fiber 33. The spectrometer 34 acquires the plasma light incident upon the optical element 32. The spectrometer 34 disperses the incident plasma light toward different directions according to wavelengths by way of a diffraction grating or a prism.

The optical detector 35 is disposed so as to receive light of a predetermined wavelength band from among the plasma lights dispersed by the spectrometer 34. The optical detector 35, in response to an instruction signal outputted from the control device 14, converts the received light of the wavelength band into an electrical signal and outputs it. As the optical detector 35, for example, a photomultiplier tube (PMT) may be employed. The electrical signal outputted from the optical detector 35 is inputted in the signal processing device 36. Any device other than the photomultiplier tube may be employed as the optical detector 35, as long as it has a high time response.

The signal processing device 36 detects time series variation in intensity of the light received by the optical detector 35 based on the electrical signal outputted from the optical detector 35. The signal processing device 36 generates information with respect to time series variation of emission intensity as shown in the graph of FIG. 3, for example.

The signal processing device 36 calculates the delay time Ts of the emission from the microwave plasma in relation to the emission from the laser plasma. The signal processing device 36 identifies the target substance 15 by using the delay time Ts.

The signal processing device 36 detects energy of the laser light that has been oscillated by the laser light source 21 based on an output value from the first power meter 31A and a separation rate of the laser light by the beam sampler 30. The signal processing device 36 detects energy of the laser light that has passed through the cavity 12 based on an output value from the second power meter 31B. The signal processing device 36 detects energy that has been absorbed by the plasma based on a difference between the energy of the laser light that has passed through the cavity 12 and the energy of the laser light that has been oscillated by the laser light source 21.

Operation of Optical Analysis Device

The optical analysis device 13 performs an optical analysis operation for analyzing the plasma light under instruction from the control device 14. The optical analysis operation is carried out in cooperation with the plasma generation and maintenance operation.

More particularly, in the optical analysis device 13, the plasma light emitted from the plasma sequentially passes through the optical element 32 and the optical fiber 33 and is incident upon the spectrometer 34. The spectrometer 34 disperses the incident plasma light toward different directions according to wavelengths. Thus, the plasma light of a predetermined wavelength band reaches the optical detector 35. The optical detector 35 converts the received plasma light of the wavelength band into an electrical signal and outputs it. The signal processing device 36 detects time series variation of the plasma light in emission intensity based on the output signal from the optical detector 35. The signal processing device 36 calculates delay time Ts of the emission from the microwave plasma in relation to the emission from the laser plasma, and identifies the target substance 15 based on the delay time Ts. The name of the identified substance is displayed on a monitor of the signal processing device 36.

The signal processing device 36 includes a memory, in which values of the delay time Ts respectively corresponding to a plurality of types of substance are stored. The values of the delay time Ts stored in the signal processing device 36 are calculated under the assumption that energy of the microwave per unit time is equivalent to the output of the microwave oscillator 23 of the first embodiment under a predetermined temperature and pressure. The signal processing device 36 reads out from the memory a type of substance corresponding to the delay time Ts and identifies the type of substance thus read out as a component of target substance 15.

The delay time Ts is calculated by using a value Ix of the emission intensity, which is greater than the minimum value Imin of the emission intensity after the peak caused by the laser plasma and less than the value Is toward which the emission intensity approximately converges due to the microwave plasma. The signal processing device 36 calculates a period starting from a point of time when the emission intensity reaches the value Ix after the emission intensity caused by the laser plasma decreases to a point of time when the emission intensity reaches the value Ix again while the emission intensity caused by the microwave plasma increases as the delay time Ts. Also, the point of time when the emission intensity reaches the peak due to the laser plasma may be determined as the starting point of the delay time Ts, or the point of time when the emission intensity reaches the minimum value Imin after the emission intensity reaches the peak due to the laser plasma as the starting point of the delay time Ts. The point of time when the emission intensity reaches a constant due to the microwave plasma may be determined as the end point of the delay time Ts, or the point of time at the inflection point when the emission intensity increases due to the microwave plasma may be determined as the end point of the delay time Ts.

Figure 4:
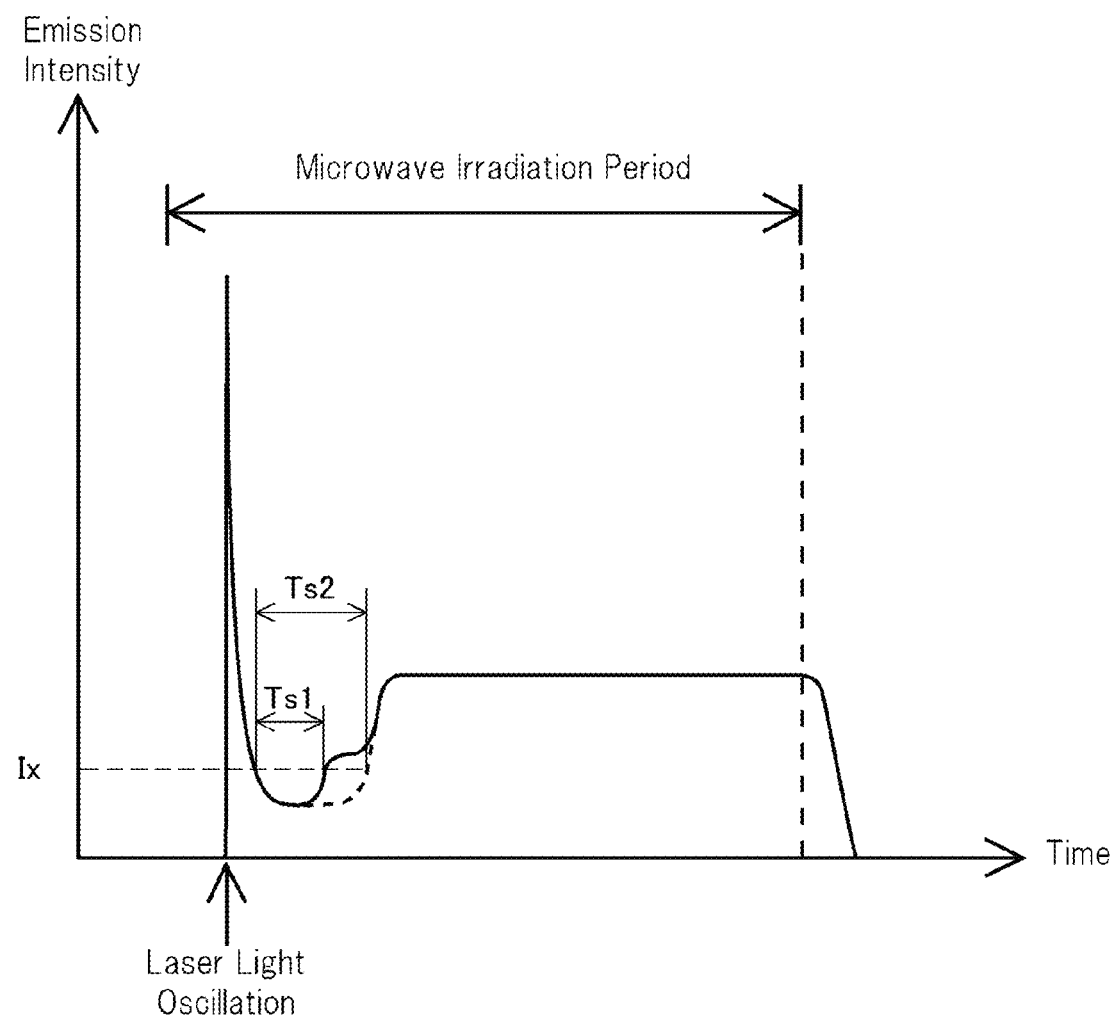
FIG. 4 is a graph showing time series variation in emission intensity of emission from plasma generated by the plasma generation device according to the first embodiment in a case in which the emission includes emissions from a plurality of types of substance.

Ina case in which emissions from a plurality of types of substance are included in the light received by the optical detector 35, the emission intensity varies stepwise while the emission intensity increases due to the microwave, as shown in FIG. 4. In such a case, it is possible to separate respective lines of emission intensity in accordance with information on changing points of emission intensity and the like, thereby detecting delay times Ts1 and Ts2 of respective lines. Thus, it is possible to identify the types of substance corresponding to respective delay times Ts1 and Ts2 as components of the target substance 15.

Effect of First Embodiment

In the first embodiment, the target substance 15 can be identified based on the information with respect to emission intensity during the period from when the emission intensity reaches the peak caused by the laser plasma until when the emission intensity increases again and reaches approximately a constant value due to the microwave plasma, since different types of substance yield different variations in emission intensity during the period from when the emission intensity reaches the peak caused by the laser plasma until when the emission intensity increases again and reaches approximately the constant value due to the microwave plasma. Accordingly, it is possible to realize the analysis apparatus 10 that can identify the target substance 15 based on variation in emission intensity of the plasma light while the plasma is being formed.

First Modified Example of First Embodiment

In a first modified example of the first embodiment, the signal processing device 36 identifies the target substance 15 based on increase rate (hereinafter, referred to as "target increase rate") of emission intensity per unit time while the emission intensity increases due to the microwave plasma immediately after the emission caused by the laser plasma. The signal processing device 36 includes a memory, in which respective values of the target increase rate corresponding to a plurality of types of substance are stored. During the optical analysis operation, the signal processing device 36 calculates the target increase rate $\Delta I/\Delta t$, reads out from the memory a type of substance corresponding to the target increase rate $\Delta I/\Delta t$ thus calculated, and identifies the type of substance thus read out as a component of the target substance 15.

As shown in FIG. 3, the period of time for which the target increase rate $\Delta I/\Delta t$ is calculated may be determined between two arbitrarily selected points of time while the emission intensity increases due to the microwave, or may be determined from the point of time when the emission intensity reaches the minimum Imin after the peak of the emission intensity caused by the laser plasma until when the emission intensity reaches the constant value due to the microwave plasma.

Second Modified Example of First Embodiment

In a second modified example of the first embodiment, the signal processing device 36 identifies the target substance 15 based on decrease rate (hereinafter, referred to as "target decrease rate") of emission intensity per unit time while the emission intensity decreases after the microwave irradiation is terminated. The signal processing device 36 includes a memory, in which respective values of the target decrease rate corresponding to a plurality of types of substance are stored. During the optical analysis operation, the signal processing device 36 calculates the target decrease rate, reads out from the memory a type of substance corresponding to the target decrease rate, and identifies the type of substance thus read out as a component of the target substance 15.

In the second modified example, the optical analysis device 13 constitutes an optical analysis unit that identifies the target substance 15 based on information with respect to the emission intensity after the electromagnetic wave irradiation is terminated.

The signal processing device 36 may identify the target substance 15 based on a period of time from when the microwave irradiation is terminated until when the emission intensity vanishes.

<Second Embodiment>

An analysis apparatus 10 according to a second embodiment is an apparatus that detects quantity and concentration of a specific substance contained in a gas, such as hydrogen, carbon monoxide, carbon dioxide, or OH radical as a target substance.

In the second embodiment, the plasma generation device 11 constitutes a plasma generation unit that energizes a target substance contained in a fluid and turns the target substance into a plasma state. The optical analysis device 13 constitutes an optical analysis unit that detects concentration and quantity of the target substance based on variation rate of emission intensity per unit time of emission caused by plasma generated by the plasma generation unit at a wavelength corresponding to the target substance.

Figure 5:
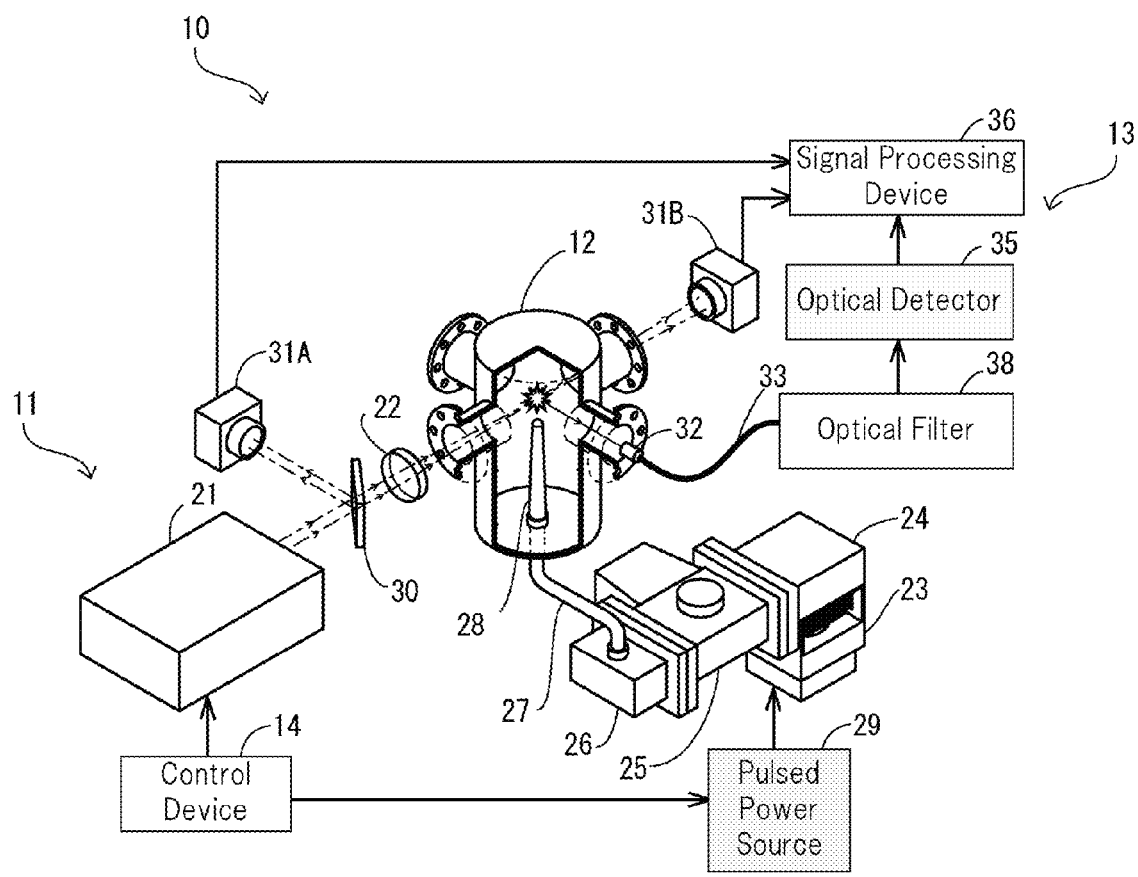
FIG. 5 is a schematic configuration diagram of an analysis apparatus according to a second embodiment.

The plasma generation device 11 has almost the same configuration as the first embodiment. In the optical analysis device 13, in place of the spectrometer 34, an optical filter 38 is employed to extract from the plasma light a light of the wavelength corresponding to the target substance, as shown in FIG. 5.

During the optical analysis operation, the plasma light emitted from the plasma sequentially passes through the optical element 32, the optical fiber 33, and the optical filter 38, and reaches the optical detector 35. The optical detector 35 receives light of the wavelength to be analyzed, which corresponds to the target substance, converts the light of the wavelength to be analyzed into an electrical signal, and outputs it. The signal processing device 36 detects time series variation in emission intensity of the light of the wavelength to be analyzed based on the output signal from the optical detector 35. The signal processing device 36 calculates decrease rate (hereinafter, referred to as "vanishing decrease rate") of emission intensity per unit time at the wavelength to be analyzed while the microwave plasma is vanishing, and detects the quantity of the target substance based on the vanishing decrease rate.

The signal processing device 36 includes a memory, in which respective values of the vanishing decrease rate corresponding to a plurality of values regarding the quantity of the target substance are stored. The values of the vanishing decrease rate stored in the signal processing device 36 are calculated under the assumption that energy of the microwave per unit time is equivalent to the output of the microwave oscillator 23 of the second embodiment under a predetermined temperature and pressure. The vanishing decrease rate decreases as the target substance increases in quantity, since time required for the plasma to vanish increases. The signal processing device 36 reads out from the memory a value of the quantity of the target substance corresponding to the detected vanishing decrease rate and determines the value thus read out as the quantity of the target substance.

Also, in the memory of the signal processing device 36, a volume of a region from which the plasma light is acquired via the optical element 32 in an area where the microwave is formed is stored. The signal processing device 36 divides the detected quantity by the volume read out from the memory, thereby calculating concentration (molar concentration) of the target substance.

The signal processing device 36 may correct the quantity calculated from the vanishing decrease rate based on the detected value of energy of the laser light oscillated by the laser light source 21, and/or may correct the quantity calculated from the vanishing decrease rate based on the detected value of energy absorbed by the plasma.

Effect of Second Embodiment

In the second embodiment, concentration and quantity of the target substance is detected based on variation rate of emission intensity per unit time of the plasma light at the analyzed wavelength, since the variation rate of emission intensity per unit time at the analyzed wavelength differs depending on concentration and quantity of the target substance. Accordingly, it is possible to realize an analysis apparatus 10 that can detect concentration and quantity of the target substance based on variation in emission intensity of the plasma light while the plasma is being formed.

Modified Example of Second Embodiment

In a modified example of the second embodiment, the signal processing device 36 detects concentration or quantity of the target substance based on the decrease rate of emission intensity per unit time of emission from the laser plasma generated by the laser light at the wavelength corresponding to the target substance. The concentration or quantity of the target substance is detected based on the decrease rate during the decay process of the emission intensity of the plasma from the peak value caused by the laser plasma.

In this case, the plasma generation device 11 is not required to maintain the plasma by the microwave, and it suffices as long as the plasma generation device 11 includes at least the laser light source 21 and the light collection optical system 22.

<Third Embodiment>

A third embodiment is different from the first and second embodiments in the initial plasma generation unit.

Figure 6:
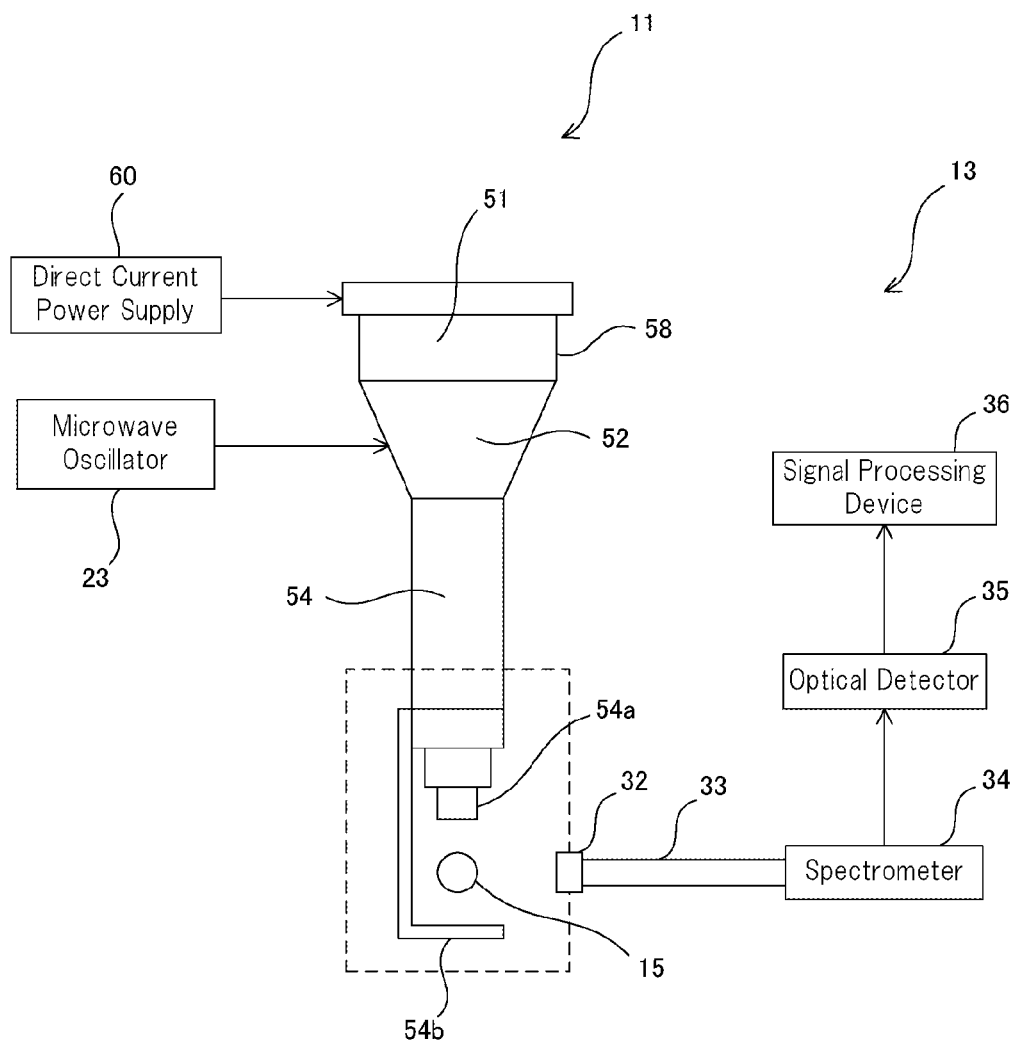
FIG. 6 is a schematic configuration diagram of an analysis apparatus according to a third embodiment.
Figure 7:
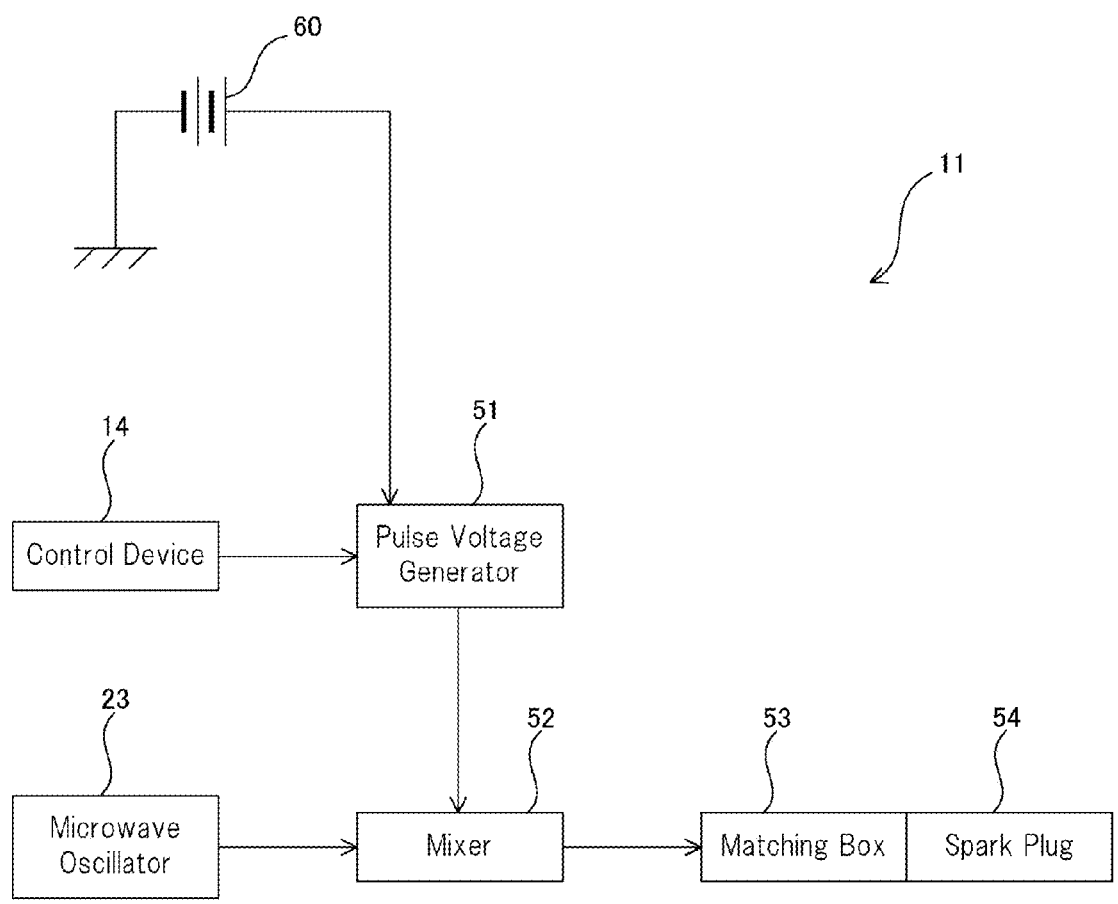
FIG. 7 is a schematic configuration diagram of a plasma generation device according to the third embodiment.

In the third embodiment, a discharge device (such as a spark plug) is employed to turn the target substance into a plasma state. More particularly, as shown in FIGS. 6 and 7, the plasma generation device 11 includes a pulse voltage generator 51, a microwave oscillator 23, a mixer 52, a matching box 53, and a spark plug 54. As shown in FIG. 6, the voltage generator 51, the mixer 52, the matching box 53, and the spark plug 54 integrally constitute a discharge unit 58 (though the matching box 53 is not illustrated in FIG. 6).

The pulse voltage generator 51 is supplied with direct current power from an outside direct current power supply 60. The pulse voltage generator 51, upon receiving a discharge signal outputted from the control device 14, generates and outputs a high pulse voltage. The pulse voltage is a pulsed voltage signal having a peak voltage of 6 kV to 40 kV, for example. Properties of the pulse voltage may be configured as appropriate so that the spark plug 54 can breakdown when the spark plug 54 is applied with the pulse voltage.

The mixer 52 receives the pulse voltage from the pulse voltage generator 51 as well as the microwave from the microwave oscillator 23. The mixer 52 generates and outputs a mixed signal of the pulse voltage and the microwave. The mixed signal is transmitted to the spark plug 54 via the matching box 53. The matching box 53 performs impedance matching of the microwave outputted from the mixer 52.

The spark plug 54 is formed with a discharge gap between a discharge electrode 54a and a ground electrode 54b. When the mixed signal is applied to the spark plug 54, a discharge occurs and a microwave is radiated. As a result thereof, small scale discharge plasma (initial plasma) is formed at the discharge gap of the spark plug 54 caused by the discharge, and the discharge plasma absorbs energy of the microwave and expands. The expanded plasma becomes a microwave plasma. The microwave is radiated for a predetermined period of time.

Although, in the third embodiment, timing to start the microwave oscillation is set before the spark discharge, the timing may be set after the spark discharge as long as the microwave oscillation starts before the discharge plasma vanishes.

In the third embodiment, as shown in FIG. 6, the target substance 15 is disposed at the discharge gap. The target substance 15 is supported by a support member (not shown).

During the plasma generation and maintenance operation, light emitted from the target substance 15 in plasma state is incident upon the optical element 32, which is disposed facing toward the target substance 15. And then, the optical analysis device 13 analyzes the target substance 15 similarly to the first and second embodiments.

<Other Embodiments>

The above described embodiments may also be configured as follows.

In the embodiments described above, as the laser light source 21, a solid state laser light source other than Nd-YAG laser light source may be employed. Also, a liquid laser light source, a gas laser light source, a semiconductor laser light source, or a free electron laser light source may be employed.

Furthermore, in the embodiments described above, the initial plasma generation unit may suffice as long as it can provide sufficient energy to cause breakdown, and may be a thermal electron generator such as glow plug, a laser diode, or a super luminosity LED other than the laser light source 21 and the spark plug 54.

Furthermore, in the embodiments described above, as the microwave oscillator 23, other types of oscillator such as a semiconductor oscillator may be employed.

INDUSTRIAL APPLICABILITY

The present invention is useful in relation to an analysis apparatus and an analysis method that analyzes a target substance by analyzing emission from plasma.

EXPLANATION OF REFERENCE NUMERALS

10 Analysis Apparatus
11 Plasma Generation Device (Plasma Generation Unit)
12 Cavity
13 Optical Analysis Device (Optical Analysis Unit)
21 Laser Light Source
22 Light Collection Optical System
23 Microwave Oscillator
28 Antenna
32 Optical Element
33 Optical Fiber

The invention claimed is:

1. An analysis apparatus, comprising:
  a plasma generation unit that generates initial plasma using a laser by momentarily energizing a target substance to be turned into a plasma state, and maintains the target substance in the plasma state by irradiating the initial plasma with an electromagnetic microwave for a predetermined period of time; and
  an optical analysis unit that identifies the target substance based on information with respect to emission intensity until when the emission intensity increases and reaches approximately a constant value due to electromagnetic wave plasma maintained by the electromagnetic microwave, or information with respect to emission intensity after the electromagnetic wave irradiation is terminated,
  wherein the optical analysis unit identifies the target substance based on delay time of emission from the electromagnetic plasma in relation to emission from the initial plasma.

2. The analysis apparatus according to claim 1, wherein the optical analysis unit identifies the target substance based on increase rate of emission intensity per unit time when the emission intensity increases due to the electromagnetic wave plasma immediately after the emission from the initial plasma.

3. An analysis apparatus, comprising:
  a plasma generation unit that generates initial plasma using a laser by momentarily energizing a target substance to be turned into a plasma state, and maintains the target substance in the plasma state by irradiating the initial plasma with an electromagnetic microwave for a predetermined period of time; and
  an optical analysis unit that identifies the target substance based on information with respect to emission intensity until when the emission intensity increases and reaches approximately a constant value due to electromagnetic wave plasma maintained by the electromagnetic microwave, or information with respect to emission intensity after the electromagnetic wave irradiation is terminated,
  wherein the optical analysis unit identifies the target substance based on increase rate of emission intensity per unit time when the emission intensity increases due to the electromagnetic wave plasma immediately after the emission from the initial plasma.

4. An analysis apparatus, comprising: a plasma generation unit that energizes a target substance contained in a fluid and turns the target substance into a plasma state by irradiating the target substance with laser and that maintains the target substance in the plasma state by irradiating the plasma with an electromagnetic microwave; and an optical analysis unit that detects at least one of concentration and quantity of the target substance based on variation rate of emission intensity per unit time of emission from the plasma generated by the plasma generation unit at a wavelength corresponding to the target substance,
  wherein the plasma generation unit includes an initial plasma generation unit that energizes the target substance and turns the target substance into a plasma state, and a plasma maintenance unit that maintains the target substance in the plasma state by irradiating initial plasma generated by the initial plasma generation unit with the electromagnetic microwave for a predetermined period of time, and the optical analysis unit detects at least one of concentration and quantity of the target substance based on decrease rate of emission intensity per unit time when the plasma vanishes after the plasma maintenance unit terminates the electromagnetic wave irradiation.

* * * * *